United States Patent [19]

Di Schiena et al.

[11] 4,405,618
[45] Sep. 20, 1983

[54] THIAZOLIDINE DERIVATIVES WITH ANTIBIOTIC ACTIVITY

[75] Inventors: Michele Di Schiena; Vittoria Orrù, both of Trezzano sul Naviglio, Italy

[73] Assignee: Ausonia Farmaceutici s.r.l., Rome, Italy

[21] Appl. No.: 279,454

[22] Filed: Jul. 1, 1981

[30] Foreign Application Priority Data

Jul. 15, 1980 [IT] Italy .................. 23455 A/80

[51] Int. Cl.³ .................. C07D 501/57; A61K 31/545
[52] U.S. Cl. .................... 424/246; 544/21; 544/16
[58] Field of Search .............. 424/246; 544/21, 16, 544/27, 28

[56] References Cited

U.S. PATENT DOCUMENTS 4,008,246 2/1977 Ochiai et al. .................. 544/21

Primary Examiner—Nicholas S. Rizzo
Attorney, Agent, or Firm—Bucknam and Archer

[57] ABSTRACT

New derivatives of 1,3-thiazolidin-4-yl carboxylic acid of the general formula I

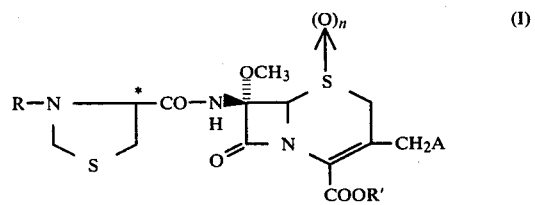

wherein
R represents hydrogen, $(C_{1-4})$alkyl, aralkyl, phenyl, phenyl substituted by a halogen atom or a methoxy group, formyl, acyl, trimethylsilyl;

R' represents hydrogen, a pharmaceutically acceptable inorganic or organic cation, $(C_{1-4})$alkyl, 2,2,2-trichloroethyl, acetonyl, benzyl, benzyl substituted by nitro or methoxy, phenyl, nitrophenyl, benzhydryl or trimethylsilyl;

R' may also represent a radical capable of providing metabolic activation in vivo selected from acetoxymethyl, pivaloyloxymethyl, phthalidyl, benzoyloxymethyl, 5-indanyl, a group of formula

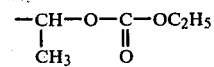

or a group of formula

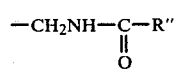

in which R" stands for $(C_{1-4})$alkyl, $(C_{5-6})$cycloalkyl or aryl; A represents hydrogen, halogen, $N_3$, OH, $NH_2$; or a quaternary N-atom, particularly

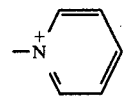

(and in this case R' is a negative charge; or a O—CO—NH$_2$ group; or a group of the formula OR'''; O—COR''', NH—CO—R''' or SR''', where R''' is $(C_1-C_4)$alkyl, aryl, substituted aryl or a heterocyclic group which can carry lower alkyls;
n may be zero or 1.

The compounds possess antibacterial utility against microbial infections in man, animals and plants.

5 Claims, No Drawings

THIAZOLIDINE DERIVATIVES WITH ANTIBIOTIC ACTIVITY

DESCRIPTION OF THE INVENTION

The present invention refers to new 1,3-thiazolidin-4-yl-carboxylic acid derivatives of the general formula I

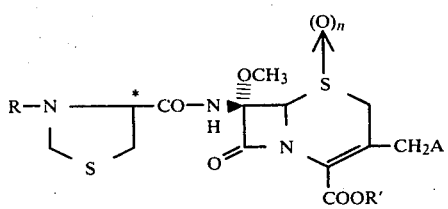

wherein:
R represents hydrogen, $(C_{1-4})$alkyl, aralkyl, phenyl, phenyl substituted by a halogen atom or a methoxy group, formyl, acyl, trimethylsilyl;
R' represents hydrogen, a pharmaceutically acceptable inorganic or organic cation, $(C_{1-4})$alkyl, 2,2,2-trichloroethyl, acetonyl, benzyl, benzyl substituted by nitro or methoxy, phenyl, nitrophenyl, benzhydryl or trimethylsilyl;
R' may also represent a radical capable of providing metabolic activation in vivo selected from acetoxymethyl, pivaloyloxymethyl, phthalidyl, benzoyloxymethyl, 5-indanyl, a group of formula

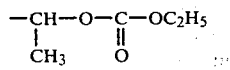

or a group of formula

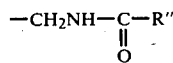

in which R" stands for $(C_{1-4})$alkyl, $(C_{5-6})$cycloalkyl or aryl;
A represents hydrogen, halogen, $N_3$, OH, $NH_2$; or a quaternary N-atom, particularly

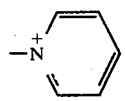

(and in this case R' is a negative charge); or a O—CO—$NH_2$ group; or a group of the formula OR''', O—COR''', NH—CO—R''' or SR''', where R''' is $(C_1-C_4)$alkyl, aryl, substituted aryl or a heterocyclic group which can carry lower alkyls;
n may be zero or 1.

Characteristic meanings assumed by the radical R besides those already illustrated above are selected from methyl, ethyl, isopropyl, benzyl, trityl, acetyl, propionyl, trifluoroacetyl, benzoyl, benzoyl substituted by one to three hydroxy, methyl, methoxy, halo, amino and nitro groups, benzyloxycarbonyl, tert.-butoxycarbonyl or a radical deriving from a natural aminoacid.

Typical, but not limitative examples of the inorganic or organic cations represented by the radical R' are sodium, potassium, calcium and magnesium cations; cations deriving from organic bases such as, for instance, dibenzylamine, N,N-dibenzylethylenediamine, glucamine, N-methylglucamine, hexamethylenetetramine, 2-amino-2-hydroxymethyl-1,3-propanediol, arginine, lysine, proline, carnitine; or aluminum, zinc or silver cations. Typical meanings of R''', besides those already illustrated above, are selected from methyl, ethyl, propyl, butyl, isobutyl; phenyl or benzyl; imidazol-2-yl, 1,2,3-triazol-5-yl, 1-methyl-1,2,3,4-tetrazol-5-yl, thiazol-2-yl, 1,3,4-thiadiazol-2-yl, 5-methyl-1,3,4-thiadiazol-2-yl, 1,2,3,4-thiatriazol-5-yl, oxazol-5yl, 3-methylisoxazol-5-yl, 1,2,4-oxadiazol-5yl, pyrazinyl. Because of the presence of the asymmetric carbon atom at the 4-position of the thiazolidine ring, the compound of formula I may exist in one of the D- and L-configuration or as a racemic compound. Accordingly the invention contemplates all of these possibilities, though the L-configuration is the preferred one.

A further object of the invention is also represented by the salts of the compounds of formula I, in which the nitrogen atom of the thiazolidine nucleus has basic character, with pharmaceutically acceptable acids, e.g. citric, ascorbic, maleic, acetic, chloridric, nitric, hydrobromic and sulfuric acid.

Another object of the invention is represented by the pharmaceutical compositions for human or veterinary use, or pesticidal formulations for agricultural use containing as the active ingredient one or more of the compounds of formula I above or a pharmaceutically acceptable acid addition salt thereof.

It has been now surprisingly found that the compounds of formula I according to the invention are highly resistant to penicillinases when tested according to the method described by GROVE et al., Assay methods of antibiotics, A Laboratory Manual, Med. Encyclop. Inc., 1955, 7, or according to LORIAN V., Antibiotics and chemotherapeutic agents in clinical and laboratory practice, C. C. Thomas Publ., 1966, 242. They also have proven to be active against various pathogenic agents, e.g. gram-positive and gram-negative, aerobes and anaerobes bacteria, including β-lactamase producing strains.

More particularly, the compounds of formula I are active against gram-positive bacteria such as, for instance, *Staphylococcus aureus*, *Diplococcus pneumoniae*, *Streptococcus pyogenes*, *Streptococcus faecalis*, *Bacillus subtilis* and *Sarccina lutea*, as well as gram-negative bacteria such as, for instance, *Escherichia coli*, *Proteus mirabilis*, *Shigella sonnei*, *Klebsiella pneumoniae*, *Pseudomonas aeruginosa*, *Haemophilus influenzae* and *Salmonella typhimurium*.

The compounds of formula I according to the invention display also a remarkable activity against various pathogenic agents responsible of infections in vegetables, e.g.: *Pseudomonas syringae*, responsible of the bacteriosis of citrus-fruits and lilacs; *Pseudomonas phaseolicola* (halo blight of beans); *Pseudomonas aliicola* (bacterial mould of onions); *Pseudomonas savastandi* (scab of olive-trees); *Pseudomonas marginata* (scab of gladiolus); *Xantomonas phaseoli* (bacterial mildew of beans); *Pectob. carotovorum* (stump of potatoes and bacterial mould of *iris rhizomes*); *Erwinia amilovora* (necrosis of orchard branches); *Erwinia carotovora* (bacterial mould of carrots); *Corynebacterium flaccum-faciens* (bacterial of beans); *Penicillum sp.* (bacterial mould of bulbs and corms).

As a representative, but not limitative example, it is reported that 7-(1,3-thiazolidin-4-yl)carboxamido7α-methoxy-3-carbamoyloxymethyl-3-cephem-4-carboxylic acid (formula I, wherein R=R'=H, A=O—CO—NH₂ and n=O), both as sodium salt and as lysine salt, is at least active, against gram-positive bacteria, as cephoxitin, and furthermore do not yields resistence on the examined strains.

Accordingly, the new compounds which are one of the objects of the present invention may be administered to warm blooded animals, including humans, by oral, parenteral or topic route for combatting septicaemiae, meningitis, endocarditis; infections of the respiratory, gastroenteric and genitourinary tract and of the skin; ear-, nose-, throat infections; infections of bones; endoabdominal and endopleurical infections. They may also be employed in the asepsis of the skin before injections or surgical interventions; as well as in the disinfection of surgical tools.

The pharmaceutical dosage forms suitable for the oral administration may be, for instance, tablets, capsules, pills, sugar coated tablets, syrups; suspensions, drops, elixirs and granules. Pharmaceutical dosage forms suitable for the topical use are essentially represented by ointments, cremes, embrocations, collyria and lotions.

All of the above mentioned pharmaceutical formulations are prepared as known in the art and contain, together with the active ingredient, lubricant, diluent, excipient, and sweetening agents as well as the commonly employed pharmaceutically acceptable additives.

In their quality of phytopharmaceuticals the compounds according to the invention can be employed in various administration forms, as an example aqueous solutions containing or not containing additional additives such as, for instance, talc or clay; powders, including the atomized preparations; sprays, both liquid and solids; suppositories, including the slow-release formulations; granules, including the slow-release formulations; the forms absorbed on inert materials or ion-exchange resins; capsules and microincapsulated preparations. All of these administration forms are well familiar to the art skilled technician.

Accordingly, the compounds of the present invention may also usefully be employed for the preservation of food-stuffs such as, for instance, citrus-fruits or potatoes; as, contrary to a lot of commonly employed substances, e.g. the bis-phenyl, they are effective antibiotic agents displaying a very low toxicity. The compounds of the invention can be prepared by different procedures. Thus, for instance, the amino group of a compound of formula II

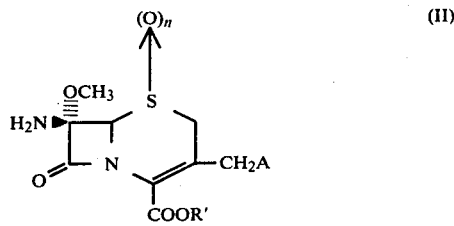

wherein R', A and n are as above defined, is acylated with a suitable N-acylating reactant deriving from an acid of formula III

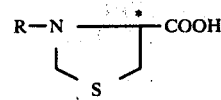

wherein R is as above defined. The protecting groups, if any, must easily be removable under mild conditions. Typical example of a protecting group is the benzyloxycarbonyl radical. Such acylation reactions are well known in the field of penicillins and cephalosporins (see, for instance, Flynn, Cephalosporins and penicyllins, Academic Press, 1972). Also the starting substances of formula II and III are known to the art skilled technician. The choice of the acylating agents will obviously depend on the chemical nature of the substituents R and R', according to the common techniques and principles.

The N-acylating reactants deriving from the compound of formual III above are, for instance, the halides or those obtained through the reaction of III with the carbodiimide or the azide; preferably, an anhydride is employed and, advantageously, a mixed anhydride prepared in situ by reaction with ethyl- or isobutyl- chlorocarbonate, or pivaloyl chloride.

The choice of the reaction solvent and conditions, which essentially depend on the selected N-acylating agent, is a familiar task for the art expert. As an example, if the acylating agent is a mixed anhydride, the reaction may be carried out in an organic solvent selected from ethyl acetate, dimethylformamide, diethyl ether, tetrahydrofuran, dioxane, methylene chloride or analogous inert solvents; the temperature may be comprised between about −40° C. and about the room temperature and, preferably, it is comprised between about −20° and −30° C.

A further advantageous methods for preparing the compounds of formula I comprises reacting the compounds of formula II and III above with silicon tetrachloride, according to Italian Patent Application No. 29445 A/77. The compounds of the invention can be isolated by means of techniques well known in the field of penicillins and cephalosporins such as, for instance, by crystallization, lyophylization or spray-drying. A suitable isolating procedure comprises the absorption on chemically inert or activated material, as an example the ion exchanging resins; this procedure may be particularly useful when the obtained derivative must be used as food for animals or as phytopharmaceuticals. The following examples are provided with the purpose of better illustrating the invention but in no way they must be construed as a limitation of the invention itself.

EXAMPLE 1

7-(1,3-Thiazolidine-4-yl)-carboxamido-7α-methoxy-3-carbamoyloxymethyl-3-cephem-4-carboxylic acid, sodium salt (compound of formula I, wherein R=H; R'=Na; A=—O—CO—NH₂; n=zero)

24.4 Grams of 7-amino-7α-methoxy-3-carbamoyloxymethyl-3-cephem-4-carboxylic acid are added to 200 ml of anhydrous CH₂Cl₂. To the stirred suspension, keeping the temperature under −25° C., 13 g of n-propylamine are added. After 30' at this temperature, 26 g of trimethylsilyl chloride are added; the temperature rises until −10° C. The mixture is stirred for 30' at this temperature, then 18.5 g of N,N-dimethylaniline and 88 g of the 1,3-thiazolidine-4-yl-carboxylic acid chloridehydrochloride are added. The mixture is then stirred for 2 hours at room temperature, then is added with 500 ml of water, stirred about 30 minutes to complete the cleavage of the trimethylsilyl group, and finally neutralized to pH 7-7.5 with diluted NaOH. The organic phase is separated and the aqueous one is washed with 100 ml of methyl isobutyl ketone, then with 100 ml of diethyl ether. The aqueous phase is stirred for 15' with 3 g of charcoal and pump filtered on a layer of "Dicalite 438". From the filtered solution the desired sodium salt is obtained by liophylisation, in form of a white powder, whose nature is confirmed by the N.M.R.-spectrum.

EXAMPLE 2

7-(1,3-Thiazolidine-4-yl)carboxamido-7α-methoxy-3-carbamoyloxymethyl-3-cephem-4-carboxylic acid, lysine salt (compound of formula I wherein R=H; R'=lysine cation; A=—O—CO—NH₂; n=O).

To a solution of 0.1 moles of lysine in 100 ml of water, 0.1 moles of 7-(1,3-thiazolidine-4-yl)-carboxamido-7α-methoxy-3carbamoyloxymethyl-3-cephem-4-carboxylic acid (obtained by treatment of the sodium salt of example 1 with ion exchangers) are added. After 1 hour at room temperature, the aqueous solution is filtered on a sterile, depyrogenating filter, and mechanically dosed in phials, such as to obtain phials containing lysine salt corresponding to 1 gram of the acid. By lyophylization, the compound is obtained in a pharmaceutical form which can be intravenously administered.

I claim:

1. An antibiotically active compound of formula I

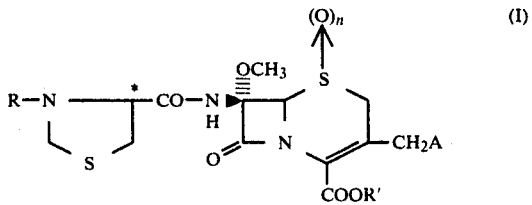

wherein
R is hydrogen;
R' is hydrogen, a pharmaceutically acceptable inorganic or organic cation;
A is O—CO—NH₂;
n is 1,
The asymmetric C-atom (*) of the thiazolidine nucleus having the D- or L-configuration or being in the racemic form.

2. Compound according to claim 1 wherein, in the formula I, R=H, R'=H, A=O—CO—NH₂, n=zero.

3. Compound according to claim 1 wherein, in the formula I, R=H, R'=Na, A=O—CO—NH₂, n=zero.

4. Compound according to claim 1 wherein, in the formula I, R=H, R'=cation of lysine, A=O—CO—NH₂, n=zero.

5. A pharmaceutical composition endowed with antibiotic activity, for human, veterinary or agricultural use, containing as the active principle at least one compound of formula I

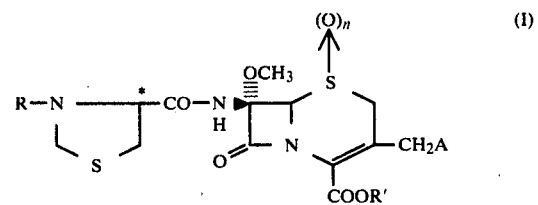

wherein
R is hydrogen;
R' is hydrogen, a pharmaceutically acceptable inorganic or organic cation;
A is O—CO—NH₂;
n is 1, the asymmetric C-atom (*) of the thiazolidine nucleus having the D- or L-configuration or being in the racemic form and at least one member selected from the group consisting of lubricants, diluents, excipients and sweetening agents.

* * * * *

UNITED STATES PATENT AND TRADEMARK OFFICE
CERTIFICATE OF CORRECTION

PATENT NO. : 4,405,618

DATED : September 20, 1983

INVENTOR(S) : Michele Di Schiena and Vittoria Orru

It is certified that error appears in the above-identified patent and that said Letters Patent are hereby corrected as shown below:

Column 6, line 16 and column 6, line 46, in both instances, delete "n is 1" and substitute therefor: --n is zero--.

Signed and Sealed this

Twenty-first Day of February 1984

[SEAL]

Attest:

GERALD J. MOSSINGHOFF

Attesting Officer

Commissioner of Patents and Trademarks